United States Patent
Garner et al.

(10) Patent No.: US 7,291,327 B2
(45) Date of Patent: Nov. 6, 2007

(54) COMPOSITIONS AND METHODS FOR INHIBITING PATHOGENIC GROWTH

(75) Inventors: Bryan E. Garner, Amarillo, TX (US); Douglas R. Ware, Indianapolis, IN (US)

(73) Assignee: Nutrition Physiology Corporation, Amarillo, TX (US)

( * ) Notice: Subject to any disclaimer, the term of this patent is extended or adjusted under 35 U.S.C. 154(b) by 426 days.

(21) Appl. No.: 10/905,216

(22) Filed: Dec. 21, 2004

(65) Prior Publication Data

US 2005/0238630 A1    Oct. 27, 2005

Related U.S. Application Data

(60) Division of application No. 10/288,487, filed on Nov. 6, 2002, now Pat. No. 7,063,836, which is a continuation of application No. 10/273,141, filed on Oct. 18, 2002, now abandoned.

(60) Provisional application No. 60/319,587, filed on Oct. 1, 2002, provisional application No. 60/319,054, filed on Jan. 8, 2002.

(51) Int. Cl.
*A61K 45/00* (2006.01)

(52) U.S. Cl. .................................................. 424/93.45
(58) Field of Classification Search .............. 424/93.45
See application file for complete search history.

(56) References Cited

U.S. PATENT DOCUMENTS

| 4,814,273 | A | * | 3/1989 | Brumm et al. | ............... | 435/140 |
| 5,529,793 | A | * | 6/1996 | Garner et al. | ................. | 426/61 |
| 7,063,836 | B2 | * | 6/2006 | Garner et al. | ............ | 424/93.45 |

* cited by examiner

*Primary Examiner*—Jon Weber
*Assistant Examiner*—Kailash C. Srivastav
(74) *Attorney, Agent, or Firm*—Novak Druce & Quigg, LLP

(57) ABSTRACT

The invention includes methods and compositions for treating an animal to inhibit the incidence and growth of *E. coli* O157:H7 and other pathogenic bacteria. The treatment method comprises administering a therapeutically effective amount of *Lactobacillus acidophilus* or one or a combination of a number of other probiotic bacteria to an animal. An alternative treatment method comprises administering a therapeutically effective amount of a lactic acid producing bacterium such as *Lactobacillus acidophilus* in combination with a lactate utilizing bacterium such as *Propionibacterium freudenreichii*.

5 Claims, No Drawings

COMPOSITIONS AND METHODS FOR INHIBITING PATHOGENIC GROWTH

CROSS REFERENCE TO RELATED APPLICATIONS

This application is a Divisional Application of U.S. patent application Ser. No. 10/288,487 filed Nov. 6, 2002 now U.S. Pat. No. 7,063,836. Said application Ser. No. 10/288,487 is a Continuation Application of U.S. patent application Ser. No.10/273,141 filed Oct. 18, 2002 now abandoned. Further, said application Ser. No. 10/288,487 claims priority to U.S. Provisional Patent Application Nos. 60/319,054 filed Jan. 8, 2002 and 60/319,587 filed Oct. 1, 2002, all applications incorporated herein by reference in their entireties.

FIELD OF THE INVENTION

The present invention relates to compositions and methods for inhibiting pathogenic growth. More specifically, the invention relates to compositions and methods for inhibiting pathogenic growth through the use of lactic acid producing microorganisms both alone and in combination with lactate utilizing microorganisms.

BACKGROUND OF THE INVENTION

Ingestion of pathogens, especially bacterial pathogens, but including viruses and other disease causing microorganisms, is a common problem in most animals. Pathogens have been known to cause illnesses in animals that have wide ranging deleterious effects including weight loss, diarrhea, abdominal cramping, and renal failure. For animals that are immunosuppressed or malnourished, even just the effects of diarrhea can be fatal. Pathogens are often transferred between animals where poor hygiene conditions exist, and sometimes communicability cannot be prevented even when great care is taken. The most common solution to this problem has been to provide antibiotics to the animals; however, this solution is not only costly, but it also can result in the generation of antibiotic-resistant strains of bacteria.

Extreme health risks result when humans consume pathogens in contaminated food products such as sprouts, lettuce, meat products, unpasteurized milk and juice, and sewage-contaminated water, for example. The problem is particularly prevalent in the beef and dairy industry. Pathogens present on a cow's udder or on milking equipment may find their way into raw milk. Meat can become contaminated during slaughter, and pathogenic organisms can be mixed into large quantities of meat when it is ground. When humans eat meat, especially ground beef, that has not been cooked sufficiently to kill any pathogens present in the beef, serious and life-threatening infections can result. This is a difficult problem to solve because contaminated meat often looks and smells perfectly normal. Furthermore, the number of pathogenic organisms needed to cause disease is extremely small, thus making detection extraordinarily difficult.

Pathogens that cause disease in the intestinal tract are known as enteropathogens. Examples of enteropathogenic bacteria, or enterobacteria, include *Staphylococcus aureus*, particular strains of *Escherichia coli* (*E. coli*), and *Salmonella* spp. Whereas most of the hundreds of strains of *E. coli* are harmless and live in the intestines of animals, including humans, some strains, such as *E. coli* O157: H7, O111: H8, and O104: H21, produce large quantities of powerful shiga-like toxins that are closely related to or identical to the toxin produced by *Shigella dysenteriae*. These toxins can cause severe distress in the small intestine, often resulting in damage to the intestinal lining and resulting in extreme cases of diarrhea. *E. coli* O157: H7 can also cause acute hemorrhagic colitis, characterized by severe abdominal cramping and abdominal bleeding. In children, this can progress into the rare but fatal disorder called hemolytic uremic syndrome ("HUS"), characterized by renal failure and hemolytic anemia. In adults, it can progress into an ailment termed thrombotic thrombocytopenic purpura ("TTP"), which includes HUS plus fever and neurological symptoms and can have a mortality rate as high as fifty percent in the elderly.

Reduction of risk for illnesses due to food borne pathogens can be achieved by controlling points of potential contamination. The beef industry has recognized the need to investigate pre-harvest control of pathogens, particularly *E. coli* O157: H7, due to potential runoff contamination, contact with humans, and the transfer of pathogens during meat processing. In particular, undercooked or raw hamburger (ground beef) has been implicated in many documented outbreaks as containing *E. coli* O157: H7.

Accordingly, there is a recognized need for compositions and methods for reducing or eliminating the growth of enteropathogens such as *E. coli* O157: H7 for the health benefits to the animals. Furthermore, there is an important need for reducing or eliminating the growth of enteropathogens in meat and milk producing animals prior to their harvest for the benefit of consumers. By such reduction or elimination in food animals, consumers of beef, dairy, and other food products will be better protected from the risk of consuming such pathogens.

SUMMARY OF THE INVENTION

Since pathogens are known to populate many distinct areas of animals' digestive tracts, it has been found to be most beneficial to supply and potentiate those organisms that occur naturally in those areas and which are effective for inhibiting pathogenic growth throughout the digestive tract, such as the rumen, small intestine, and large intestine. The present invention identifies such naturally occurring organisms suitable for serving this purpose and demonstrates methods for enhancing their populations and efficacy. The microorganisms in the formulations and methods of the present inventions may individually and collectively produce compounds that inhibit the growth of pathogens in the gastrointestinal tract ("GIT") of animals. By inhibiting the growth of the pathogens, the methods and compounds of the invention provide a reduced likelihood of contaminated food products resulting from treated animals.

The invention exploits the natural competition of certain microorganisms with the pathogenic organisms that it is the object of the invention to reduce or destroy. The microorganisms in the formulations of the invention may exhibit multifaceted modes of action. These actions range from complex actions such as acting as or producing bactericides to simply competing with the pathogen by using more nutrients and attachment spaces than the pathogens, thus preventing them from becoming established within the GIT. These advantageous action modes can be contrasted with less advantageous techniques conventionally known for achieving such effects as using aseptic husbandry accompanied by the addition of antibiotics and like substances to animals' feed.

In the competitive mode of action, particularly of *Lactobacillus acidophilus*, including strain 381-IL-28 (also known as and referred to throughout as the LA51 strain and NPC747), the microorganisms out-grow and out-populate *E. coli* O157: H7, thereby acting as an inhibitor to that pathogen. *E. coli* O157: H7 and *Lactobacillus acidophilus* are understood to at least partly utilize the same limited supply of in vitro nutrients such as sugar. Furthermore, these microorganisms compete for the same attachment space: on the lining of the GIT. With a rapid-proliferation inhibitor such as *Lactobacillus acidophilus*, the primary mode of action against *E. coli* O157: H7 is to overwhelm it by using the available food and suitable attachment spaces.

The invention includes a method of treating or preventing an intestinal pathogenic infection in a ruminant comprising administering to the ruminant a composition comprising a therapeutically effective amount of a lactic acid producing bacterium, wherein the lactic acid producing bacterium reduces the quantity of a pathogen in the intestine of the ruminant. In one embodiment, the lactic acid producing bacterium is selected from the group consisting of: *Bacillus subtilis, Bifidobacterium adolescentis, Bifidobacterium animalis, Bifidobacterium bifidum, Bifidobacterium infantis, Bifidobacterium longum, Bifidobacterium thermophilum, Lactobacillus acidophilus, Lactobacillus agilis, Lactobacillus alactosus, Lactobacillus alimentarius, Lactobacillus amylophilus, Lactobacillus amylovorans, Lactobacillus amylovorus, Lactobacillus animalis, Lactobacillus batatas, Lactobacillus bavaricus, Lactobacillus bifermentans, Lactobacillus bifidus, Lactobacillus brevis, Lactobacillus buchnerii, Lactobacillus bulgaricus, Lactobacillus catenaforme, Lactobacillus casei, Lactobacillus cellobiosus, Lactobacillus collinoides, Lactobacillus confusus, Lactobacillus coprophilus, Lactobacillus coryniformis, Lactobacillus corynoides, Lactobacillus crispatus, Lactobacillus curvatus, Lactobacillus delbrueckii, Lactobacillus desidiosus, Lactobacillus divergens, Lactobacillus enterii, Lactobacillus farciminis, Lactobacillus fermentum, Lactobacillus frigidus, Lactobacillus fructivorans, Lactobacillus fructosus, Lactobacillus gasseri, Lactobacillus halotolerans, Lactobacillus helveticus, Lactobacillus heterohiochii, Lactobacillus hilgardii, Lactobacillus hordniae, Lactobacillus inulinus, Lactobacillus jensenii, Lactobacillus jugurti, Lactobacillus kandleri, Lactobacillus kefir, Lactobacillus lactis, Lactobacillus leichmannii, Lactobacillus lindneri, Lactobacillus malefermentans, Lactobacillus mali, Lactobacillus maltaromicus, Lactobacillus minor, Lactobacillus minutus, Lactobacillus mobilis, Lactobacillus murinus, Lactobacillus pentosus, Lactobacillus plantarum, Lactobacillus pseudoplantarum, Lactobacillus reuteri, Lactobacillus rhamnosus, Lactobacillus rogosae, Lactobacillus tolerans, Lactobacillus torquens, Lactobacillus ruminis, Lactobacillus sake, Lactobacillus salivarius, Lactobacillus sanfrancisco, Lactobacillus sharpeae, Lactobacillus trichodes, Lactobacillus vaccinostercus, Lactobacillus viridescens, Lactobacillus vitulinus, Lactobacillus xylosus, Lactobacillus yamanashiensis, Lactobacillus zeae, Pediococcus acidlactici, Pediococcus pentosaeus, Streptococcus cremoris, Streptococcus discetylactis, Streptococcus faecium, Streptococcus intermedius, Streptococcus lactis, Streptococcus thermophilus*, and combinations thereof. In one embodiment, the lactic acid producing bacterium is *Lactobacillus acidophilus*. In another embodiment, the *Lactobacillus acidophilus* strains include the M35, LA45, LA51 and L411 strains. In another embodiment, the *Lactobacillus acidophilus* strain is LA51. The lactic acid producing bacterium may be administered at a level of at least $1 \times 10^8$ CFU/day. Alternatively, the lactic acid producing bacterium may be administered at a level of about $1 \times 10^9$ CFU/day. The pathogen may be selected from the group consisting of *E. coli, Salmonella* spp., including *Salmonella typhirium*, and *Staphylococcus aureus*. Alternatively, the pathogen may be *E. coli* O157: H7.

Another aspect of the invention includes a composition for treating or preventing a pathogenic infection in a ruminant comprising a *Lactobacillus acidophilus* strain selected from the group consisting of M35, LA45, LA51 and L411 in combination with animal feed. In one embodiment, the *Lactobacillus acidophilus* strain is LA45 or LA51. In another embodiment, the *Lactobacillus acidophilus* strain is LA51. The *Lactobacillus acidophilus* may be present in the animal feed in an amount of greater than $1 \times 10^8$ CFU for each quantity of food equal to the amount eaten by one animal in one day, or the *Lactobacillus acidophilus* may be present in the animal feed in an amount of about $1 \times 10^9$ CFU for each quantity of food equal to the amount eaten by one animal in one day.

As already mentioned, strain LA51 is also known as 381-IL-28, and is available under that accession number from the Oklahoma State University collection. While the inventors have characterized LA51 as a *Lactobacillus acidophilus*, other means of characterization have identified it as *Lactobacillus animalis*, and *Lactobacillus murinus*. LA45 is deposited at the American Type Culture Collection under accession number ATCC 53545. M35 and L411 are the accession numbers for those bacteria available from the University of Nebraska.

Another aspect of the invention includes a method of treating or preventing an intestinal pathogenic infection in a ruminant, the method comprising administering to the ruminant a composition comprising a therapeutically effective amount of a lactic acid producing bacterium and a lactate utilizing bacterium, wherein the lactic acid producing bacterium reduces the quantity of a pathogen in the intestine of the ruminant. The lactic acid producing bacterium may be selected from the group consisting of: *Bacillus subtilis, Bifidobacterium adolescentis, Bifidobacterium animalis, Bifidobacterium bifudum, Bifidobacterium infantis, Bifidobacterium longum, Bifidobacterium thermophilum, Lactobacillus acidophilus, Lactobacillus agilis, Lactobacillus alactosus, Lactobacillus alimentarius, Lactobacillus amylophilus, Lactobacillus amylovorans, Lactobacillus amylovorus, Lactobacillus animalis, Lactobacillus batatas, Lactobacillus bavaricus, Lactobacillus bifermentans, Lactobacillus bifidus, Lactobacillus brevis, Lactobacillus buchnerii, Lactobacillus bulgaricus, Lactobacillus catenaforme, Lactobacillus casei, Lactobacillus cellobiosus, Lactobacillus collinoides, Lactobacillus confusus, Lactobacillus coprophilus, Lactobacillus coryniformis, Lactobacillus corynoides, Lactobacillus crispatus, Lactobacillus curvatus, Lactobacillus delbrueckii, Lactobacillus desidiosus, Lactobacillus divergens, Lactobacillus enterii, Lactobacillus farciminis, Lactobacillus fermentum, Lactobacillus frigidus, Lactobacillus fructivorans, Lactobacillus fructosus, Lactobacillus gasseri, Lactobacillus halotolerans, Lactobacillus helveticus, Lactobacillus heterohiochii, Lactobacillus hilgardii, Lactobacillus hordniae, Lactobacillus inulinus, Lactobacillus jensenii, Lactobacillus jugurti, Lactobacillus kandleri, Lactobacillus kefir, Lactobacillus lactis, Lactobacillus leichmannii, Lactobacillus lindneri, Lactobacillus malefermentans, Lactobacillus mali, Lactobacillus maltaromicus, Lactobacillus minor, Lactobacillus minutus, Lactobacillus mobilis, Lactobacillus murinus, Lactobacillus pentosus, Lactobacillus plantarum, Lactobacillus pseudoplantarum, Lactobacillus reuteri, Lactobacillus rhamnosus, Lactobacillus rogosae, Lactobacillus tolerans, Lactobacillus torquens, Lactobacillus ruminis, Lactobacil-* lus sake, Lactobacillus salivarius, Lactobacillus sanfrancisco, Lactobacillus sharpeae, Lactobacillus trichodes, Lactobacillus vaccinostercus, Lactobacillus viridescens, Lactobacillus vitulinus, Lactobacillus xylosus, Lactobacillus yamanashiensis, Lactobacillus zeae, Pediococcus acid-lactici, Pediococcus pentosaceus, Streptococcus cremoris, Streptococcus discetylactis, Streptococcus faecium, Streptococcus intermedius, Streptococcus lactis, Streptococcus thermophilus, and combinations thereof. The lactate utilizing bacterium may be selected from the group consisting of Megasphaerae eilsdenii, Peptostreptococcus asaccharolyticus, Propionibacterium freudenreichii, Propionibacterium acid-propionici, Propionibacterium freudenreichii, Propionibacterium globosum, Propionibacterium jensenii, Propionibacterium shermanii, Propionibacterium spp., Selenomonas ruminantium, and combinations thereof. In one embodiment, the lactic acid producing bacterium is Lactobacillus acidophilus. In another embodiment, the Lactobacillus acidophilus strain is selected from the group consisting of M35, LA45, LA51 and L411. In another embodiment, the Lactobacillus acidophilus is the LA51 strain. In one embodiment, the lactate utilizing bacterium is Propionibacterium freudenreichii. In another embodiment, the Propionibacterium freudenreichii strain is selected from the group consisting of P9, PF24, P42, P93 and P99. In another embodiment, the Propionibacterium freudenreichii strain is PF24, available from the ATCC under accession number ATCC 9615. The lactate utilizing bacterium and the lactic acid producing bacterium may each be administered in an amount of greater than $1\times10^8$ CFU/day, or in an amount of about $1\times10^9$ CFU/day. Alternatively, the lactate utilizing bacterium may be administered in an amount of about $1\times10^6$ CFU/day. In another embodiment the lactate utilizing bacterium is administered in an amount of greater than $1\times10^6$ CFU/day, preferably in an amount of greater than $1\times10^8$ CFU/day, and most preferably in an amount of about $1\times10^9$ CFU/day.

Another aspect of the invention includes a composition for treating or preventing a pathogenic infection in a ruminant comprising a Lactobacillus acidophilus strain selected from the group consisting of M35, LA45, LA51, L411, and combinations thereof, in combination with a Propionibacterium freudenreichii strain selected from the group consisting of P9, PF24, P42, P93, P99, and combinations thereof. In one embodiment, the composition further comprises animal feed. In another embodiment, the Lactobacillus acidophilus and the Propionibacterium freudenreichii are each present in the animal feed in an amount of greater than $1\times10^8$ CFU for each quantity of food equal to the amount eaten by one animal in one day. In another embodiment, the Lactobacillus acidophilus strain LA51 and Propionibacterium freudenreichii strain PF24 are each present in the animal feed in an amount of about $1\times10^9$ CFU for each quantity of food equal to the amount eaten by one animal in one day. In another embodiment, the composition further comprises Lactobacillus acidophilus strain LA45 present in the animal feed in an amount of about $1\times10^6$ CFU for each quantity of food equal to the amount eaten by one animal in one day.

DETAILED DESCRIPTION OF THE INVENTION

The present invention provides methods and compositions for reducing or eliminating the growth of pathogens in the gut of an animal. In vitro and in vivo tests have been conducted utilizing certain strains of microorganisms, which have been found to be particularly effective at inhibiting the growth of many pathogens, including E. coli O157: H7. As used herein, the term "pathogens" refers to any bacterium that produces a harmful effect in a host animal, and especially those bacteria that infect meat and dairy animals and subsequently infect the human food supply, thus causing disease in humans. The invention is considered to be useful in preventing the growth of a wide variety of pathogenic organisms, as demonstrated herein by several tests showing the inhibition of growth of pathogenic bacteria including E. coli, Salmonella spp., including Salmonella typhirium, and Staphylococcus aureus.

The formulations and methods described herein are applicable to a wide variety of animal species and commercial practices. The inhibition of pathogens in the GIT of animals may be considered for those used in the commercial production of meat, milk, poultry, and fish. In one aspect, the invention includes a method for treating an animal to inhibit the incidence and growth of E. coli O157: H7. The treatment method includes administering a therapeutically effective amount of a selected Lactobacillus acidophilus to an animal that inhibits in vivo growth of E. coli O157: H7. As used herein, the term "therapeutically effective amount" refers to the quantity of bacteria administered to an animal that results in a therapeutic effect by creating an inhospitable environment for pathogens. It has been found that a therapeutically effective amount of Lactobacillus acidophilus can be as little as $1\times10^6$ CFU/day when it is administered in combination with other components, although it is preferable that the lactic acid producing bacteria of the invention are administered in an amount of greater than $1\times10^8$ CFU/day. It has been found to be particularly effective when the selected Lactobacillus acidophilus is administered at a level of approximately $1\times10^9$ CFU/day.

Among the Lactobacillus acidophilus strains found to be particularly effective as E. coli O157: H7 inhibitors is the 381-IL-28, or the LA51 strain. In one aspect, the invention includes Lactobacillus acidophilus strains that are effective compositions in the above-described methods when provided as a product in the prescribed concentrations for animal consumption as E. coli O157: H7 inhibitors. Before the present invention, Lactobacillus acidophilus microorganisms had been administered as animal feed additives for different purposes such as better utilization of feed-stuffs. For example, U.S. Pat. Nos. 5,534,271 and 5,529,793 (incorporated herein by reference), report that certain combinations of lactic acid producing bacteria and lactate utilizing bacteria could be used in a method to improve the utilization of feedstuffs by ruminants. The present invention, by contrast, sets forth methods for inhibiting pathogenic growth in animals and for improving the quality and quantity of dairy products. However, one aspect of the present invention includes the discovery that certain novel formulations for inhibiting pathogenic growth disclosed herein are also useful for improving the utilization of feedstuffs. To the extent that these formulations were previously unknown for improving utilization of feedstuffs, they form part of the present invention for that purpose.

In one embodiment, the present invention includes a method for providing a product as an inhibitor of E. coli O157: H7 growth in animals. The method includes selecting a therapeutically effective microorganism as an E. coli O157: H7 inhibitor in animals and producing a product containing this microorganism. Generally, such products require government approval to be certified as pathogen inhibitors; specifically, certification from the United States Department of Agriculture (USDA) is typically required. If the product is for human consumption, for example to counteract an *E. coli* infection in a human, approval by the United States Food and Drug Administration (FDA) is required.

An example of a microorganism found to be therapeutically effective is *Lactobacillus acidophilus*, preferably the LA51 strain, which inhibits in vivo growth of *E. coli* O157: H7 and other pathogenic microorganisms when administered to animals at a dose of approximately $1\times10^9$ CFU/day. Alternatively, a sufficient level may be considered to be at least as much as $1\times10^8$ CFU/day. Exact dosage levels can easily be determined by those skilled in the art by evaluating the bile tolerance of the bacteria to be administered in order to verify that viable organisms are delivered to the intestinal tract to compete with and inhibit the growth of pathogenic bacteria such as *E. coli* O157: H7.

The present invention identifies several naturally occurring organisms that are capable of inhibiting pathogen growth within the GIT of an animal. Since many pathogens are acid resistant and populate many distinct areas of an animal's digestive tract, the naturally occurring organisms of the invention are preferably capable of inhibiting pathogen growth at a lower pH and in several areas of the GIT; e.g., the rumen, small intestine and large intestine. Earlier research has shown that *E. coli* O157: H7 populations may be decreased in cattle by feeding hay rations, which in and of itself increases rumen pH to 7.0. However, this has limited application in the finishing or feedlot industries since animals in this phase of the production process are typically fed a diet that has a greater proportion of grain in order to foster better carcass characteristics.

Microorganisms that are useful in the formulations and methods of the present invention may be capable of producing lactic acid in the GIT. These microorganisms include, for example, the genera *Lactobacillus* or *Enterococcus*. Either or both genera may be used. They are distinguished by their ability to utilize sugars such as glucose or lactose or, in the case of *Enterococcus*, to utilize starch, to produce lactic acid, and thus reduce the local pH level. The choice of microorganism can depend upon the locus at which the desired effect is to be given. For example, the genus *Lactobacillus* is capable of reducing local pH more than *Enterococcus* microorganisms.

Lactic acid producing organisms that may be used in the methods and compositions of the invention include but are not limited to: *Bacillus subtilis, Bifidobacterium adolescentis, Bifidobacterium animalis, Bifidobacterlum bifudum, Bifidobacterlum infantis, Bifidobacterlum longum, Bifidobacterium thermophilum, Lactobacillus acidophilus, Lactobacillus agilis, Lactobacillus alactosus, Lactobacillus alimentarius, Lactobacillus amylophilus, Lactobacillus amylovorans, Lactobacillus amylovorus, Lactobacillus animalis, Lactobacillus batatas, Lactobacillus bavaricus, Lactobacillus bifermentans, Lactobacillus bifidus, Lactobacillus brevis, Lactobacillus buchnerii, Lactobacillus bulgaricus, Lactobacillus catenaforme, Lactobacillus casei, Lactobacillus cellobiosus, Lactobacillus collinoides, Lactobacillus confusus, Lactobacillus coprophilus, Lactobacillus coryniformis, Lactobacillus corynoides, Lactobacillus crispatus, Lactobacillus curvatus, Lactobacillus delbrueckii, Lactobacillus desidiosus, Lactobacillus divergens, Lactobacillus enterii, Lactobacillus farciminis, Lactobacillus fermentum, Lactobacillus frigidus, Lactobacillus fructivorans, Lactobacillus fructosus, Lactobacillus gasseri, Lactobacillus halotolerans, Lactobacillus helveticus, Lactobacillus heterohiochii, Lactobacillus hilgardii, Lactobacillus hordniae, Lactobacillus inulinus, Lactobacillus jensenii, Lactobacillus jugurti, Lactobacillus kandleri, Lactobacillus kefir, Lactobacillus lactis, Lactobacillus leichmannii, Lactobacillus lindneri, Lactobacillus malefermentans, Lactobacillus mali, Lactobacillus maltaromicus, Lactobacillus minor, Lactobacillus minutus, Lactobacillus mobilis, Lactobacillus murinus, Lactobacillus pentosus, Lactobacillus plantarum, Lactobacillus pseudoplantarum, Lactobacillus reuteri, Lactobacillus rhamnosus, Lactobacillus rogosae, Lactobacillus tolerans, Lactobacillus torquens, Lactobacillus ruminis, Lactobacillus sake, Lactobacillus salivarius, Lactobacillus sanfrancisco, Lactobacillus sharpeae, Lactobacillus trichodes, Lactobacillus vaccinostercus, Lactobacillus viridescens, Lactobacillus vitulinus, Lactobacillus xylosus, Lactobacillus yamanashiensis, Lactobacillus zeae, Pediococcus acidlactici, Pediococcus pentosaceus, Streptococcus cremoris, Streptococcus discetylactis, Streptococcus faecium, Streptococcus intermedius, Streptococcus lactis, Streptococcus thermophilus*.

In one aspect of the invention, any of the above listed lactic acid producing microorganisms may be used to inhibit or treat infections of a host of pathogens, particularly bacterial pathogens including pathogenic bacteria such as *Escherichia coli, Staphylococcus aureus*, and *Salmonella* spp., including *Salmonella typhirium*. These lactic acid producing microorganisms are particularly useful for inhibiting or treating infections of *E. coli* O157: H7. It has also been found that these organisms may be used for improving the performance of food animals by increasing carcass weight, carcass quality, reducing carcass pathogens, and increasing average daily weight gain and feed efficiency ratio. Any one of these microorganisms may be used for any of these purposes, or any combination of these microorganisms may be used.

In another aspect, the invention includes a formulation of a combination of lactic acid producing microorganisms, such as those described in the preceding paragraphs, with a second microorganism that enhances the effectiveness of the lactic acid producing microorganisms in competing with pathogenic microorganisms. Enhancing microorganisms that may be used in the formulations of the present invention are preferably lactate utilizing microorganisms. Examples of lactate utilizing microorganisms useful in the present invention include but are not limited to: *Megasphaerae eilsdenii, Peptostreptococcus asaccharolyticus, Propionibacterium freudenreichii, Propionibacterium acid-propionici, Propionibacterium freudenreichii, Propionibacterium globosum, Propionibacterium jensenii, Propionibacterium shermanii, Propionibacterium* spp., and *Selenomonas ruminantium*. A therapeutically effective amount of these enhancing microorganisms is a quantity that produces a beneficial therapeutic effect in the animal to which they are administered, for example, a therapeutically effective amount of these enhancing microorganisms may be greater than $1\times10^6$ CFU/day, preferably $1\times10^8$ CFU/day, or even more preferably about $1\times10^9$ CFU/day.

The use of specific microorganisms ensures that the desired effect is produced locally. The different microorganisms used in the formulation should be compatible with each other, for example, capable of growing together, and preferably, potentiating the other. Additionally, the microorganisms preferably grow fast at the locus of action. The microorganisms may be selected for various characteristics, such as resistance to bile acids and/or commercial antibiotics, that make them most suited for their intended use.

In a preferred mode, the formulations of the invention include *Lactobacillus acidophilus, Lactobacillus crispatus*, or *Lactobacillus murinus*, either individually or in any combination. In another preferred mode, the formulations of the invention include *Lactobacillus acidophilus, Lactobacillus crispatus,* or *Lactobacillus murinus,* either individually or in any combination with each other, and additionally include *Propionibacterium freudenreichii* or *Propionibacterium shermanii* or both. Preferably, the formulations of the invention are applied to the daily feed of beef or dairy cattle in a dry supplement, or in a liquid spray applied to the daily feed of the animals. The formulations may be administered once a day or over the course of a day, either in one meal, or divided among the meals, or in any other suitable way.

IN VITRO TESTS

EXAMPLES 1 AND 2

Several in vitro tests were conducted that demonstrate the ability of particular bacteria to effectively compete with and interfere with the growth of pathogenic bacteria such as *E. coli* O157: H7 and others.

EXAMPLE 1

Lyophilized cultures of lactic acid producing and lactate utilizing organisms were selected for their ability to inhibit the growth of pathogens such as *E. coli* O157: H7, *Streptococcus aureus* and *Salmonella*. Combinations of the lactic acid producing and lactate utilizing organisms were further selected for their ability to maximize the inhibition of growth of the various pathogens.

In order to identify those microorganisms that might be utilized in the method and formulation of the invention, in vitro tests were conducted to identify particularly effective single strains. Seven strains of *Propionibacterium* and six strains of *Lactobacillus* were screened for their ability to produce bacteriocins capable of creating zones of inhibition on agar plates that were grown with *E. coli* O157: H7. The results of those tests are tabulated below.

TABLE 1

Inhibitory Activity of *Propionibacterium* Strains Grown in Selective Media

|  | P9 | P42 | P79 | P88 | P93 | P99 | PF24 |
|---|---|---|---|---|---|---|---|
| PATHOGEN Gram + |  |  |  |  |  |  |  |
| B. cereus | No | No | No | No | No | No | No |
| S. aureus | Yes | Yes | Yes | No | No | No | No |
| Gram − |  |  |  |  |  |  |  |
| E. coli O157:H7 | Yes | Yes | No | No | Yes | Yes | Yes |
| Sal. typhirium | No | Yes | No | Yes | Yes | Yes | Yes |

TABLE 2

Inhibitory Activity of *Lactobacillus* Strains Grown in Selective Media

|  | 30SC | 53545 | 381IL28 | C28 | FR3 | R2 |
|---|---|---|---|---|---|---|
| PATHOGEN |  |  |  |  |  |  |
| E. coli 43985 O157:H7 | −4.1 | 16.8 | 91.8 | 89.7 | 88.7 | 64.9 |
| E. coli 933 O157:H7 | 28.1 | −3.4 | 92.7 | 93.5 | 91 | 89.4 |
| S. aureus 305 | −15.6 | −22.1 | 82.6 | 80.6 | 84.8 | 23.3 |

From the above tables, it may be appreciated that three strains of *Lactobacillus* lactic acid producing organisms—381IL28, C28 and FR3—and four strains of *Propionibacterium* lactate utilizing organisms—P9, P42, P93 and P99—demonstrate the ability to inhibit the growth of pathogens, in particular, *E. coli* O157: H7. It should be recognized that combinations of lactic acid producing and lactate utilizing microorganisms can be selected for their ability to maximize the inhibition of growth of various pathogens.

EXAMPLE 2

Selected strains of *Lactobacillus acidophilus* and *Propionibacterium freudenreichii* bacteria were grown in an in vitro comparison with *E. coli* on rich semi-anaerobic media at 38° C. to determine which strains could effectively complete with *E. coli* growth under in vivo growth conditions. It was found that the LA51 and LA45 strains could substantially out-grow the *E. coli*.

TABLE 3

Growth (Optical Density) of Selected Strains of Bacteria versus *E. coli* O157:H7 on Rich Semi-Anaerobic Media at 38° C.

| MINUTES | E. coli O157:H7 | LA45 | LA51 | PF24 |
|---|---|---|---|---|
| 0 | 0.2 | 0.2 | 0.2 | 0.2 |
| 50 | 0.3 | 0.38 | 0.55 | 0.3 |
| 90 | 0.45 | 0.65 | 0.84 | 0.35 |
| 120 | 0.60 | 0.85 | 1.0 | 0.36 |
| 200 | 0.80 | 1.2 | 1.28 | 0.38 |
| 230 | 0.85 | 1.25 | 1.28 | 0.39 |
| 365 | 0.90 | 1.25 | 1.28 | 0.50 |
| 440 | 0.90 | 1.25 | 1.28 | 0.58 |

In VIVO TESTS

EXAMPLES 3-9

In the following in vivo studies, ruminants were inoculated by providing a sufficient quantity of the bacterial strains tested along with necessary growth medium components to the ruminants' intestines by normal ingestion. Inhibited growth of pathogens such as *E. coli* O157: H7 were observed in feedlot and dairy cattle, as well as other ruminants such as sheep, goats and game. Various inoculation processes were utilized. Examples of these inoculation processes include:

Placing lyophilized cultures in water, and then spraying or blending the mixture onto the feed of the animal. The mixture can be in dry form, together with additional carriers that are added to the diet of the animal. The diet can include one or more ingredients such as corn, cereal grains, corn byproducts, cereal grain byproducts, alfalfa hay, corn silage, small grain silage, grass hay, plant stalks, oilseed byproducts, protein meals, urea, minerals, molasses, and various fat and oil products.

Suspending lyophilized cultures in various oils, water and/or compounds for providing a drench to be supplied directly to the animal and the digestive tract of the animal.

Adding the lyophilized cultures to the drinking water of the animals.

EXAMPLE 3

In vivo tests were conducted with combinations of lactic acid producing and lactate utilizing microorganisms for the inhibition of the pathogen E. coli OP157: H7. The results of those tests are tabulated below in Tables 4 and 5.

TABLE 4

Inhibition of E. coli O157:H7 in Manure at 37° C.

| TREATMENT | 0 Hours | 24 Hours |
|---|---|---|
| Control | 5.74 | 6.56 |
| Combination PF24, LA45, LA51 | 5.74 | 4.48 |

TABLE 5

Inhibition of E. coli O157:H7 in Rumen Fluid at 37° C.

| TREATMENT | 0 Hours | 24 Hours | 48 Hours |
|---|---|---|---|
| Control | 6.64 | 6.70 | 6.79 |
| Combination PF24, LA45, LA51 | 5.56 | 5.04 | 5.00 |

The data is reported at $\log_{10}$ CFU E. coli O157: H7/ml. The organisms PF24, LA45 and LA51 are all able to function at a pH of about 4.0 to about 5.0 up to above a pH of about 7.0. In beef production, the chief concern is inhibiting pathogens of cattle on a finishing diet containing high levels of concentrate that tend to decrease rumen pH from about 7.0 to the range of about 5.0 to about 6.9, a range in which the formulation of the present invention preferably functions. While the above in vivo tests illustrate the use of the lactate utilizing organism PF24 and the lactic acid producing organisms LA45 and LA51, it should be understood that the present invention is not limited to these organisms as there are many strains that can be adapted for the formulation and method of the invention.

In vivo testing has also been conducted with single strains for assessing their effectiveness of pathogen growth inhibition, including E. coli O157: H7. In particular, M35 and LA51 each demonstrate the ability to inhibit shedding of E. coli O157: H7 by about fifty percent above the level of the control animals.

EXAMPLE 4

One hundred and eighty (180) cattle were sorted by weight and put into pens of five (5) animals per pen. During weighing, a fecal sample was taken directly from the rectum of each animal. Initially, only 3 of the 180 animals tested positive for E. coli O157: H7. The animals were monitored for shedding on a bi-weekly basis by taking a composite sample from five fresh droppings on the floor of each pen. Two weeks after the sorting period, twenty-five (25) of the thirty-six (36) pens, or 69%, were positive for E. coli O157: H7. Four weeks after sorting, the prevalence had declined to seven pens that were positive, or 19.4%.

With approximately sixty days left in the feeding period, the cattle were weighed, resorted, and individual animals were again tested for shedding of the pathogen. A total of twenty-six (26) animals, or 14.4%, were shedding the pathogen. The animals were re-sorted based on weight and shedding pattern. Animal treatment began at this time.

Two separate treatments utilizing two separate types of lactic acid producing bacteria (NPC 747 and NPC 750) were administered to test their ability to reduce E. coli O157: H7 in the study animals.

Pen tests taken one week following the beginning of the treatment period indicated that 25% of the pens receiving no treatment were positive for E. coli O157: H7, while 8% of the pens receiving NPC 750 treatment were positive and 0% of the pens receiving NPC 747 treatment were positive. Two weeks after the treatments, 50% of the samples taken from the control (untreated) animals were positive, while only 30% and 20% of the samples from animals receiving NPC 750 and NPC 747 treatments, respectively, were positive for E. coli O157: H7. The tests indicate a reduction in the shedding rate by approximately one-half that of the control for those receiving NPC 747 treatment, which was a greater reduction than for those receiving NPC 750 treatment. All animals shedding E. coli O157: H7 prior to receiving NPC 747 treatment tested negative after receiving the treatment. Furthermore, the pathogen did not spread to other animals in the same pen. The majority of the control animals that tested positive at the beginning of the administration of the treatment continued to test positive, with other animals in the same pen beginning to shed the pathogen.

On day 42, there were significant ($P<0.05$) differences among treatments for the individual animal samples. Ten percent (10%) of the animals fed the NPC 747 strain were positive, whereas 20% of the animals fed NPC 750 were positive. In contrast, 58% of the control animals were positive.

The animals were sampled pre-slaughter. The animals receiving NPC 747 treatment had significantly ($P<0.05$) less detectable E. coli O157: H7 with only 3.3% of the animals testing positive. The animals receiving the NPC 750 strain and those in the control group were not significantly different, with 15% and 20% shedding, respectively.

Fecal samples taken in the slaughter plant indicated that 3.3% of the NPC 747 treated animals were positive, 6.6% of the NPC 750 treated animals were positive, and 10% of the control animals were positive. Averaging all samples over all sampling times, 61.7% of the control animals shed the pathogen during the feeding period, 51.7% of the NPC 750 animals shed the pathogen, and only 35% of the NPC 747 treated animals shed the pathogen.

EXAMPLE 5

One hundred (100) steers were placed into pens of ten (10) animals per pen. Initially, a fecal sample was taken directly from the rectum of two steers per pen. Another sample was taken 170 days later. The same animals were sampled during both sampling times. A control group receiving no treatment was included in the study. The animals that were treated were treated with the Lactobacillus acidophilus strain LA51 (purchased under the trade name NPC2000). All groups were fed Rumensin and Tylan. The results of the assays are tabulated below.

TABLE 6

Inhibition of E. coli Treated with NPC 2000

| TREATMENT | Initial E. coli + | % + | Second E. coli + | % + | Final E. coli + | % + |
|---|---|---|---|---|---|---|
| Control | 2 of 20 | 10 | 4 of 20 | 20 | 3 of 20 | 15 |
| LA51 | 5 of 20 | 25 | 0 of 20 | 0 | 0 of 20 | 0 |

TABLE 7

Animal Performance Data After 198 Days (Final Results)

| TREATMENT | Initial Live Weight, lbs. | Final Live Weight, lbs. | Hot Carcass Weight, lbs. | Average Daily Weight Gain, lbs. |
|---|---|---|---|---|
| Control | 772 | 1560 | 945 | 3.98 |
| LA 51 | 772 | 1626 | 984 | 4.31 |
| Response, lb. | | 66 | 39 | 0.33 |
| % Response | | 4.23 | 4.12 | 8.30 |

EXAMPLE 6

A study was conducted to determine whether food-grade probiotic bacteria could reduce fecal shedding of E. coli O157: H7 in experimentally infected weaned beef calves. The probiotic bacteria in the study included various bovine fecal Lactobacillus spp. isolates that were selected on the basis of high-level in vitro toxic activity against E. coli O157: H7.

Five 7-month old beef calves were subjected to rumen cannulation surgery and, following recovery, housed in biosafety level 3 isolation rooms. The calves were inoculated intra-ruminally once daily for a sixty-day period with $1\times10^9$ CFU of one of the probiotic bacterial strains listed in Table 8 below.

Two weeks after initiation of probiotic administration, the calves were challenged by intra-ruminal inoculation with E. coli O157: H7 (C1). Fifteen (C2) and twenty seven (C3) days after the first inoculation (C1), the calves were again challenged. The first inoculation C1 comprised a total of about $1\times10^9$ CFU of a combination of strains 920, 922, 944 and 966. The second inoculation C2 was with a total of about $1.63\times10^{11}$ CFU of these strains. The third inoculation C3 included about $1\times10^9$ CFU of strain 86-24.

Prior to and after each challenge, the calves were tested daily for fecal shedding of the inoculum strains. Every two weeks, the animals were tested for evidence of immunity as assessed by serum antibody titers to the Tir protein and O157 lipopolysaccharide (LPS) antigen. The results are shown in Table 8 below. All calves prior to challenge had a relatively high anti-Tir antibody titer that provided the calves with a significant level of immunity against the challenge strains, as all calves, including the control, had a S:C ratio of less than one following the first C1 and second C2 treatments.

TABLE 8

Comparison of the Effect of Feeding Different Lactobacillus spp. Probiotic Strains on E. coli O157:H7 Shedding in Weaned Beef Calves

| Probiotic strain and time of challenge | Antibody Titers | | No. Days of Shedding | Total Shedding | Shedding:Challenge Ratio |
|---|---|---|---|---|---|
| | Tir | O157 | | | |
| M35 | | | | | |
| C1 | 1:12,800 | 1:12,800 | 3 | $1.45 \times 10^6$ (S1) | 0.00145 (S1/C1) |
| C2 | 1:12,800 | 1:12,800 | 2 | $3.59 \times 10^6$ (S2) | 0.000022 (S2/C2) |
| C3 | 1:12,800 | 1:12,800 | 3 | $3.14 \times 10^8$ (S3) | 0.314469 (S3/C3) |
| Total | 1:51,200 | 1:51,200 | 8 | $3.2 \times 10^8$ (S) | 0.001936 (S/C) |
| LA45 | | | | | |
| C1 | 1:6,400 | 1:12,800 | 3 | $1.8 \times 10^6$ (S1) | 0.0017955 (S1/C1) |
| C2 | 1:6,400 | 1:12,800 | 2 | $5.13 \times 10^6$ (S2) | 0.0000031 (S2/C2) |
| C3 | 1:6,400 | 1:12,800 | 19 | $1.84 \times 10^{11}$ (S3) | 184.4 (S3/C3) |
| Total | 1:12,800 | 1:51,200 | 24 | $1.84 \times 10^{11}$ (S) | 1.1759 (S/C) |
| PBS | | | | | |
| C1 | 1:25,600 | 1:12,800 | 2 | $1.0 \times 10^4$ (S1) | 0.001 (S1/C1) |
| C2 | 1:25,600 | 1:12,800 | 1 | $1.47 \times 10^9$ (S2) | 0.009 (S2/C2) |
| C3 | 1:25,600 | 1:12,800 | 8 | $2.07 \times 10^8$ (S3) | 0.207 (S3/C3) |
| Total | ND | 1:51,200 | 11 | $1.87 \times 10^9$ (S) | 0.01 (S/C) |
| LA51 | | | | | |
| C1 | 1:6,400 | 1:12,800 | 2 | $9.41 \times 10^6$ (S1) | 0.0009405 (S1/C1) |
| C2 | 1:6,400 | 1:12,800 | 1 | $5.13 \times 10^6$ (S2) | 0.0000031 (S2/C2) |
| C3 | ND | 1:12,800 | 9 | $2.62 \times 10^8$ (S3) | 0.26163 (S3/C3) |
| Total | 1:6,400 | 1:51,200 | 12 | $2.63 \times 10^8$ (S) | 0.0015944 (S/C) |

TABLE 8-continued

Comparison of the Effect of Feeding Different
*Lactobacillus* spp. Probiotic Strains on *E. coli* O157:H7
Shedding in Weaned Beef Calves

| Probiotic strain and time of challenge | Antibody Titers | | No. Days of Shedding | Total Shedding | Shedding:Challenge Ratio |
|---|---|---|---|---|---|
| | Tir | O157 | | | |
| L411 | | | | | |
| C1 | 1:12,800 | 1:6,400 | 2 | $1.03 \times 10^4$ (S1) | 0.001026 (S1/C1) |
| C2 | 1:12,800 | 1:6,400 | 8 | $6.44 \times 10^8$ (S2) | 0.0039529 (S2/C2) |
| C3 | 1:12,800 | 1:6,400 | 4 | $5.13 \times 10^9$ (S3) | 0.0513 (S3/C3) |
| Total | 1:51,200 | 1:25,600 | 14 | $6.97 \times 10^9$ (S) | 0.0042221 (S/C) |

The shedding/challenge ratio in the above table represents the total amount of *E. coli* O157: H7 shed after inoculation. This number normalizes the values allowing more accurate comparison of the animals and providing more meaningful information than just reviewing the total number of days the cattle shed the organism. M35, LA45, LA51 and L411 represent the various *Lactobacillus* strains tested. PBS represents the control animal. The total shedding is the CFU per gram in feces times the fecal output in grams on a positive day of shedding times the total number of positive days of shedding.

Because the anti-Tir titers were not significantly different among the calves, three of the four probiotics have an effect based upon the following reduction in the S:C ratio compared to the control—80% for the calf feed M35, 84% for the calf fed LA51, and 58% for the calf feed 411. Further, the animals fed M35 experienced a 27% reduction in the number of days of shedding compared to the control J3. However, in the animal fed LA51, there was a 9% increase in the number of days of shedding compared to the control J3. Accordingly, feeding probiotics is effective in the reduction of *E. coli* O157: H7 fecal shedding in cattle.

EXAMPLE 7

A study was conducted to determine whether combinations of lactate utilizing and lactic acid producing bacteria added to the feed of dairy cows could reduce pathogens in and improve the milk production of dairy cows. Three sets of dairy cows were tested. The first set of dairy cows was the control group (Group 1). The second set of dairy cows were administered the lactate utilizing bacterium *Propionibacterium freudenreichii* strain PF24 in combination with the lactic acid producing bacterium *Lactobacillus acidophilus* strain NPC 747 in accordance with the methods set forth in the preceding sections (Group 2). The third set of dairy cows were administered the lactate utilizing bacterium *Propionibacterium freudenreichii* strain PF24 in combination with two stains of the lactic acid producing bacterium *Lactobacillus acidophilus*, LA51 (NPC747) and LA45, in accordance with the methods set forth in the preceding sections (Group 3). The results of this study are set forth in table 9.

Table 9 demonstrates the effects of each of the treatment regimes on the milk production, body weight, and feed consumption of the dairy cows. The data demonstrates that treatments involving feeding the dairy cows lactate utilizing bacteria in combination with lactic acid producing bacteria resulted in statistically significant improvements in the quantity of milk produced, the quantity of fat corrected milk produced (i.e., milk with a higher fat content is weighted more), the ratio of fat corrected milk produced per quantity of feed consumed, the quantity of energy corrected milk produced (i.e., milk with a higher calorie content is weighted more), the quantity of energy corrected milk produced per quantity of feed consumed, the quantity of milk fat in the milk produced, and the urea content of the cows' blood serum. The addition of the LA45 strain in Group 3 resulted in an increase in the urea content of the cows' blood serum.

TABLE 9

The Effect of Addition of Bacterial Cultures on
Performance Variables for Lactating Dairy Cows

| Variable | Treatments | | | Standard Error | Treatment Contrasts (P < 0.10) | |
|---|---|---|---|---|---|---|
| | Group 1 | Group 2 | Group 3 | | Group 1 vs. Groups 2 and 3 | Group 2 vs. Group 3 |
| DMI[2], kg/day | 25.5 | 26.2 | 26.3 | 0.5 | NS[1] | NS |
| Milk, kg/day | 37.7 | 39.6 | 38.5 | 0.7 | 0.08 | NS |
| FCM[3], kg/day | 34.9 | 37.8 | 37.6 | 0.8 | 0.007 | NS |
| Milk/DMI, kg/kg | 1.45 | 1.53 | 1.48 | 0.04 | NS | NS |
| FCM/DMI, kg/kg | 1.35 | 1.45 | 1.44 | 0.03 | 0.03 | NS |
| ECM[4], kg/day | 34.5 | 36.8 | 37.0 | 0.8 | 0.03 | NS |
| ECM/DMI, kg/kg | 1.34 | 1.42 | 1.41 | 0.04 | 0.03 | NS |
| Milk fat, % | 3.19 | 3.23 | 3.40 | 0.10 | NS | NS |

TABLE 9-continued

The Effect of Addition of Bacterial Cultures on
Performance Variables for Lactating Dairy Cows

| | Treatments | | | | Treatment Contrasts (P < 0.10) | |
|---|---|---|---|---|---|---|
| Variable | Group 1 | Group 2 | Group 3 | Standard Error | Group 1 vs. Groups 2 and 3 | Group 2 vs. Group 3 |
| Milk fat, kg/day | 1.15 | 1.27 | 1.29 | 0.04 | 0.02 | NS |
| Milk protein, % | 2.95 | 2.94 | 3.00 | 0.05 | NS | NS |
| Milk protein, kg/day | 1.09 | 1.13 | 1.12 | 0.03 | NS | NS |
| Somatic cells/ml, x1000 | 259 | 198 | 257 | 111 | NS | NS |
| Final Body Weight, kg | 667.6 | 658.3 | 664.1 | 6.5 | NS | NS |
| Body Weight Change, kg | 28.9 | 20.8 | 21.2 | 7.3 | NS | NS |
| Serum urea N, mg/dl | 22.62 | 20.43 | 21.66 | 0.48 | 0.01 | 0.08 |
| Serum glucose, mg/dl | 64.73 | 67.55 | 65.52 | 1.19 | NS | NS |

[1]Not statistically significant for P > 0.10
[2]Dry matter intake
[3]3.5% fat-corrected milk
[4]Energy-corrected milk for comparison on an equivalent calorie basis Table 10 shows a marked reduction in the occurrence of the pathogen *E. coli* O157: H7 in fecal samples from each of the sets of dairy cows to which the combination of lactate utilizing bacteria and lactic acid producing bacteria were administered. The effect was particularly pronounced in the dairy cows administered both the LA51 (NPC747) and LA45 strains of *L. acidophilus* in combination with the PF24 strain of *P. freudenreichii*. In this set of cows, no *E. coli* O157: H7 was detected in any fecal samples.

TABLE 10

Occurrence of *E. coli* O157:H7
in Fecal Samples from Dairy Cows

| | Group 1 | Group 2 | Group 3 |
|---|---|---|---|
| *E. coli* O157:H7 occurrence | 19% | 12% | 0% |

EXAMPLE 8

A study was conducted to determine whether particular novel combinations of bacteria could reduce the occurrence of pathogenic bacteria. It was also found that these combinations improved the feeding efficiency of cattle. Two hundred forty (240) steers were assigned to 48 pens of five head each. The average weight of the steers was 780 lbs. Each pen was allotted one of four treatments: (1) group 1 was the control group and was fed no microorganisms, (2) group 2 was fed two strains: *Propionibacterium freudenreichii* strain PF24 and *Lactobacillus acidophilus* strain LA51 (NPC747), each strain in an amount of $1 \times 10^9$ CFU/day, (3) group 3 was fed three strains: PF24 in an amount of $1 \times 10^9$ CFU/day, LA51 (NPC747) in an amount of $1 \times 10^9$ CFU/day, and *Lactobacillus acidophilus* strain LA45 in an amount of $1 \times 10^6$ CFU/day, and (4) group 4 was fed three strains: PF24 in an amount of $1 \times 10^9$ CFU/day, LA51 (NPC747) in an amount of $1 \times 10^6$ CFU/day, and *Lactobacillus acidophilus* strain LA45 in an amount of $1 \times 10^6$ CFU/day.

Table 11 demonstrates an improvement in the feeding efficiencies of the groups administered the novel combinations of bacteria. All of the groups administered the novel combinations of bacteria exhibited a greater average daily weight gain over the course of 56 and 140 days relative to the control group.

TABLE 11

Feed Efficiencies

| | Average Over Days 0–56 | | Average Over Days 0–140 | |
|---|---|---|---|---|
| | Average Daily Gain | Feed Intake | Average Daily Gain | Feed Intake |
| Group 1 (control) | 4.42 lbs. | 19.16 lbs. | 3.62 lbs. | 18.82 lbs. |
| Group 2 | 4.52 lbs. | 19.62 lbs. | 3.70 lbs. | 19.32 lbs. |
| Group 3 | 4.54 lbs. | 19.24 lbs. | 3.72 lbs. | 18.79 lbs. |
| Group 4 | 4.61 lbs. | 19.61 lbs. | 3.69 lbs. | 19.31 lbs. |

Table 12 demonstrates a substantial improvement in the quantity of *E. coli* O157: H7 found in the carcasses and hides of the steers following slaughter. Notably, the carcasses of the steers in Group 2 exhibited less than half of this pathogen than the control group, and the carcasses of the steers in the other two groups also exhibited a substantial reduction in the quantity of this pathogen. Particularly notable is the dramatic reduction in the quantity of *E. coli* in the hides of all of the steers who were administered the formulations of the invention.

TABLE 12

*E. coli* O157:H7 incidence

| | Carcass | Hide |
|---|---|---|
| Group 1 (control) | 33.3% | 20% |
| Group 2 | 13.3% | 0% |
| Group 3 | 26.6% | 0% |
| Group 4 | 20% | 0% |

EXAMPLE 9

A study was conducted to determine which of several methods of controlling pathogenic growth in cattle was superior. The first method involved feeding the bacteria NPC 747 and NPC 750 (also known as M35, available under that name from the University of Nebraska) to cattle. The second method involved removing starch from the cattle's diet. The third method involved pen cleaning. The study design was 3 H 2 H 2 factorial. A finishing diet (33% high moisture corn, 20% dry rolled corn, 40% wet corn gluten feed, and 7% alfalfa, with vitamins, minerals, Rumensin, and Tylan) was fed to 432 steers (average weight 340 kg) in 54 pens, with 8 steers in each pen. The bacteria NPC 747 and NPC 750 was fed daily to the cattle in 18 pens. Half the pens were cleaned monthly, and the other half were cleaned only at the end of the study. Two weeks prior to slaughter, the diet was changed for half the cattle, with corn bran replacing corn in the cattle's feed.

Neither the first nor third methods affected steer performance ($P>0.39$), but diet change reduced DMI ($P<0.001$; 12.8 kg/d versus 11.5 kg/d) during the last two weeks, and reduced ADG and efficiency for the entire feeding period ($P<0.001$). Carcass weight was reduced 8.4 kg by diet change.

Individual fecal samples were obtained monthly and 0, 1, and 2 weeks prior to slaughter and analyzed for *E. coli* O157: H7. An entire pen was the experimental detection unit, and a pen was deemed positive for *E. coli* O157: H7 if any of the 8 steers was positive. Overall detection of *E. coli* O157: H7 was low (145/3024 animal-weeks). The second and third methods had no effect on *E. coli* O157: H7 prevalence. The first method numerically reduced *E. coli* O157 positive pens the week of marketing (44% versus 17%; $P=0.10$).

While various embodiments of the invention have been described above, it should be understood that they have been presented by way of example only, and not limitation. Thus, the breadth and scope of the present invention should not be limited by any of the above-described exemplary embodiments, but should be defined only in accordance with the following claims and their equivalents.

What is claimed is:

1. A composition to treat or inhibit a pathogenic bacterium causing a pathogenic infection in a ruminant, wherein the composition comprised of a *Lactobacillus acidophilus* strain selected from the Group consisting of C28, L411, LA51, M35 and combinations thereof in combination with a *Propionibacterium freudenreichii* strain selected from the Group consisting of P9, P42, PF24 and combinations thereof is administered to said ruminant at $10^6$-$10^9$ colony forming units (i.e., CFU) per day of said *Lactobacillus acidophilus* strain and at $10^6$-$10^9$ CFU per day of said *Propionibacterium freudenreichii* strain to eliminate, or inhibit said pathogenic infection, wherein said pathogenic bacteria are selected from the group consisting of *Escherichia coli*, *Escherichia coli* O157: H7, *Salmonella* Spp., *Salmonella typhimurium*, *Shigella* Spp., and *Staphylococcus aureus*.

2. The composition of claim 1, further comprising animal feed or water.

3. The composition of claim 2, wherein the *Lactobacillus acidophilus* and the *Propionibacterium freudenreichii* are each present in the animal feed or water in an amount of $10^8$-$10^9$ CFU for each quantity of food or water equal to the amount eaten or drunk by one ruminant animal in one day.

4. The composition of claim 2 comprising *Lactobacillus acidophilus* strain LA51 and *Propionibacterium freudenreichii* Strain PF24 each present in the animal feed or water in an amount of about $10^9$ CFU for each quantity of food or water equal to the amount eaten or drunk by one ruminant animal in one day.

5. The composition of claim 4, further comprising *Lactobacillus acidophillus* strain C28 present in the animal feed in an amount of about $10^6$ CFU for each quantity of food or water equal to the amount eaten or drunk by one ruminant animal in one day.

* * * * *